(12) United States Patent
Backman et al.

(10) Patent No.: US 9,314,164 B2
(45) Date of Patent: Apr. 19, 2016

(54) METHOD OF USING THE DETECTION OF EARLY INCREASE IN MICROVASCULAR BLOOD CONTENT TO DISTINGUISH BETWEEN ADENOMATOUS AND HYPERPLASTIC POLYPS

(71) Applicants: NORTHSHORE UNIVERSITY HEALTHSYSTEM, Evanston, IL (US); NORTHWESTERN UNIVERSITY, Evanston, IL (US)

(72) Inventors: Vadim Backman, Chicago, IL (US); Hemant Roy, Chestnut Hill, MA (US); Young L. Kim, Skokie, IL (US); Michael Siegel, Seattle, WA (US); Vladimir Turzhitsky, Evanston, IL (US)

(73) Assignees: NORTHWESTERN UNIVERSITY, Evanston, IL (US); NORTHSHORE UNIVERSITY HEALTH SYSTEM, Evanston, IL (US)

( * ) Notice: Subject to any disclaimer, the term of this patent is extended or adjusted under 35 U.S.C. 154(b) by 415 days.

(21) Appl. No.: 13/839,234

(22) Filed: Mar. 15, 2013

(65) Prior Publication Data
US 2013/0303861 A1 Nov. 14, 2013

Related U.S. Application Data

(63) Continuation-in-part of application No. 11/604,653, filed on Nov. 27, 2006, now abandoned, and a continuation-in-part of application No. 11/261,452, filed on Oct. 27, 2005.

(60) Provisional application No. 60/801,947, filed on May 19, 2006.

(51) Int. Cl.
*A61B 5/00* (2006.01)
*A61B 5/0205* (2006.01)
(Continued)

(52) U.S. Cl.
CPC ............. *A61B 5/0205* (2013.01); *A61B 5/0084* (2013.01); *A61B 5/0261* (2013.01);
(Continued)

(58) Field of Classification Search
CPC .................... A61B 2562/0233; A61B 5/0075; A61B 5/0084; A61B 5/0091; A61B 5/0205; A61B 5/0261; A61B 5/14535; A61B 5/1459; A61B 5/4255
See application file for complete search history.

(56) References Cited

U.S. PATENT DOCUMENTS 4,414,980 A 11/1983 Mott
4,582,067 A * 4/1986 Silverstein et al. ............ 600/455
(Continued)

FOREIGN PATENT DOCUMENTS

JP A-08-299310 11/1996
JP A-2000-325294 11/2000
(Continued)

OTHER PUBLICATIONS

Oct. 24, 2013 Office Action issued in U.S. Appl. No. 12/350,955.
(Continued)

*Primary Examiner* — Mark Remaly
(74) *Attorney, Agent, or Firm* — Oliff PLC

(57) ABSTRACT

The present invention, in one aspect, relates to a method for distinguishing between possible adenomatous and hyperplastic polyps using what is referred to as "Early Increase in microvascular Blood Supply" (EIBS) that exists in tissues that are close to, but are not themselves, the abnormal tissue.

37 Claims, 11 Drawing Sheets

(51) Int. Cl.
  *A61B 5/026* (2006.01)
  *A61B 5/145* (2006.01)
  *A61B 5/1455* (2006.01)
  *A61B 5/1459* (2006.01)

(52) U.S. Cl.
  CPC ......... *A61B5/14535* (2013.01); *A61B 5/14551* (2013.01); *A61B 5/4255* (2013.01); *A61B 5/0075* (2013.01); *A61B 5/0091* (2013.01); *A61B 5/1459* (2013.01); *A61B 5/14546* (2013.01); *A61B 2562/0233* (2013.01)

(56) References Cited

U.S. PATENT DOCUMENTS

| | | |
|---|---|---|
| 5,769,076 A | 6/1998 | Maekawa et al. |
| 5,799,656 A | 9/1998 | Alfano et al. |
| 5,830,132 A | 11/1998 | Robinson |
| 5,885,224 A | 3/1999 | Yoshida |
| 5,954,658 A | 9/1999 | Gorti |
| 5,974,338 A | 10/1999 | Asano et al. |
| 5,993,843 A | 11/1999 | Sakurada et al. |
| 6,091,984 A | 7/2000 | Perelman et al. |
| 6,174,291 B1 | 1/2001 | McMahon et al. |
| 6,233,470 B1 | 5/2001 | Tsuchiya |
| 6,320,184 B1 | 11/2001 | Winklhofer et al. |
| 6,364,829 B1 | 4/2002 | Fulghum |
| 6,366,726 B1 | 4/2002 | Wach et al. |
| 6,381,018 B1 | 4/2002 | Bigio et al. |
| 6,404,497 B1 | 6/2002 | Backman et al. |
| 6,432,918 B1 | 8/2002 | Winslow |
| 6,485,413 B1 | 11/2002 | Boppart et al. |
| 6,510,330 B1 | 1/2003 | Enejder |
| 6,556,853 B1 | 4/2003 | Cabib et al. |
| 6,571,118 B1 | 5/2003 | Utzinger et al. |
| 6,590,660 B2 | 7/2003 | Jung et al. |
| 6,624,890 B2 | 9/2003 | Backman et al. |
| 6,630,673 B2 | 10/2003 | Khalil et al. |
| 6,639,674 B2 | 10/2003 | Sokolov et al. |
| 6,662,031 B1 | 12/2003 | Khalil et al. |
| 6,697,652 B2 | 2/2004 | Georgakoudi et al. |
| 6,701,181 B2 | 3/2004 | Tang et al. |
| 6,707,556 B2 | 3/2004 | Turner et al. |
| 6,718,189 B2 | 4/2004 | Rohrscheib et al. |
| 6,749,565 B2 | 6/2004 | Chudner |
| 6,751,490 B2 | 6/2004 | Esenaliev et al. |
| 6,784,981 B1 | 8/2004 | Roche et al. |
| 6,802,813 B2 | 10/2004 | Schutt |
| 6,912,412 B2 | 6/2005 | Georgakoudi et al. |
| 6,922,583 B1 | 7/2005 | Perelman et al. |
| 7,186,789 B2 | 3/2007 | Hossainy et al. |
| 2002/0042558 A1 | 4/2002 | Mendelson |
| 2002/0084417 A1 | 7/2002 | Khalil et al. |
| 2002/0135752 A1 | 9/2002 | Sokolov et al. |
| 2003/0032885 A1 | 2/2003 | Rubinstein et al. |
| 2003/0036751 A1 | 2/2003 | Anderson et al. |
| 2003/0163049 A1 | 8/2003 | Balas |
| 2003/0191368 A1 | 10/2003 | Wang et al. |
| 2003/0212316 A1 | 11/2003 | Leiden et al. |
| 2003/0232445 A1 | 12/2003 | Fulghum et al. |
| 2003/0236458 A1 | 12/2003 | Hochman et al. |
| 2004/0044287 A1 | 3/2004 | Lin et al. |
| 2004/0092824 A1 | 5/2004 | Stamnes et al. |
| 2004/0146907 A1 | 7/2004 | Smith |
| 2004/0147843 A1 | 7/2004 | Bambot et al. |
| 2004/0152984 A1 | 8/2004 | Crutchfield et al. |
| 2004/0236186 A1 | 11/2004 | Chu |
| 2004/0242976 A1 | 12/2004 | Abreu |
| 2004/0249274 A1 | 12/2004 | Yaroslavsky et al. |
| 2006/0089556 A1 | 4/2006 | Bambot et al. |
| 2007/0161854 A1 | 7/2007 | Alamaro et al. |
| 2007/0173718 A1 | 7/2007 | Richards-Kortum et al. |
| 2007/0179368 A1 | 8/2007 | Backman et al. |
| 2008/0221437 A1 | 9/2008 | Agro et al. |
| 2008/0275321 A1 | 11/2008 | Furman |

FOREIGN PATENT DOCUMENTS

| | | |
|---|---|---|
| JP | A-2000-325295 | 11/2000 |
| JP | A-2001-204683 | 7/2001 |
| JP | A-2002-505900 | 2/2002 |
| JP | A-2002-535027 | 10/2002 |
| JP | A-2003-510112 | 3/2003 |
| JP | A-2003-512085 | 4/2003 |
| JP | A-2005-515473 | 5/2005 |
| WO | WO 00/42912 | 7/2000 |
| WO | WO 01/22741 A2 | 3/2001 |
| WO | WO 2007/136880 A2 | 11/2007 |

OTHER PUBLICATIONS

Office Action issued Apr. 12, 2013 in related U.S. Appl. No. 11/604,653.
Jul. 31, 2009 Office Action issued in U.S. Appl. No. 11/261,452.
Wali, R.K., et al., "Increased Mucosal Blood Flow is an Early Marker for Colon Carcinogenesis", AGA Abstracts, Undated, p. A-4.
Office Action issued in U.S. Appl. No. 12/350,955 dated May 8, 2014.
May 19, 2014 Notification of the Second Office Action issued in Chinese Patent Application No. 201080011157.4 (with English translation).
Apr. 30, 2014 Notice of Rejection issued in Japanese Patent Application No. 2011-545474 (with English translation).
Roy, Hemant K., et al., "Inducible Nitric Oxide Synthase (iNOS) Mediates the Early Increase of Blood Supply (EIBS) in Colon Carcinogenesis", Federation of European Biochemical Societies Lett., Aug. 7, 2007, pp. 3857-3862, vol. 581, No. 20, Elsevier B.V.
Jun. 23, 2014 Office Action issued in U.S. Appl. No. 11/261,452.
Sep. 2, 2014 Decision of a Patent Grant issued in Japanese Patent Application No. 2009-512139 (with English translation).
Aug. 15, 2013 Office Action issued in U.S. Appl. No. 11/261,452.
Aug. 30, 2013 Office Action issued in U.S. Appl. No. 11/604,653.
Jan. 14, 2013 Office Action issued in U.S. Appl. No. 11/604,659.
Aug. 9, 2012 Office Action issued in U.S. Appl. No. 11/604,659.
Jun. 21, 2010 Office Action issued in U.S. Appl. No. 11/604,659.
Sep. 22, 2009 Restriction/Election issued in U.S. Appl. No. 11/604,659.
Feb. 12, 2013 Office Action issued in U.S. Appl. No. 11/261,452.
Jul. 8, 2011 Office Action issued in U.S. Appl. No. 11/261,452.
Nov. 10, 2010 Office Action issued in U.S. Appl. No. 11/261,452.
Dec. 30, 2009 Office Action issued in U.S. Appl. No. 11/261,452.
Mar. 2, 2012 Office Action issued in U.S. Appl. No. 12/350,955.
Oct. 31, 2011 Office Action issued in U.S. Appl. No. 12/350,955.
Aug. 18, 2011 Office Action issued in U.S. Appl. No. 11/604,653.
Jan. 21, 2011 Office Action issued in U.S. Appl. No. 11/604,653.
May 5, 2010 Office Action issued in U.S. Appl. No. 11/604,653.
Jul. 23, 2009 Office Action issued in U.S. Appl. No. 11/604,653.
Apr. 7, 2010 International Search Report issued in corresponding Application No. PCT/US10/02556.
Wali, Ramesh, et al., "Increased Mucosal Blood Flow is an Early Marker for Colon Carcinogenesis", Gastroenterology, 124(4), Supp. 1, Apr. 2003, p. A4 (Abstract).
Backman, V., et al., "Polarized Light Scattering Spectroscopy for Quantitative Measurement of Epithelial Cellular Structures In Situ", IEEE J. of Selected Topics in Quantum Electronics, vol. 5, No. 4, Jul./Aug. 1999, pp. 1019-1026.
Backman, V., "Measuring Cellular Structure at Submicrometer Scale With Light Scattering Spectroscopy", IEEE J. of Selected Topics in Quantum Electronics, vol. 7, No. 6, Nov./Dec. 2001, pp. 887-893.
Bigio, I.J. et al., "Ultraviolet and Visible Spectroscopies for Tissue Diagnostics: Flourescense Spectroscopy and elastic-Scattering Sectroscopy", Phys. Med. Biol., vol. 42, 1997, pp. 803-814.
Cerussi, A.E., et al., "Spectroscopy Enhances the Information Content of Optical Mammography", J. of Biomed. Optics, vol. 7., No. 1, Jan. 2002, pp. 60-71.
Demos, S.G., et al., "Optical Polarization Imaging", Applied Optics, vol. 36, No. 1, Jan. 1, 1997, pp. 150-155.
Georgakoudi, I., et al., "Flouresence Reflectance, and Light Scattering Spectroscopy for Evaluating Dysplasia in Patients with Barrett's Esophagus", Gastroenterology, vol. 120, 2001, pp. 1620-1629.

(56) References Cited

OTHER PUBLICATIONS

Finlay, JC, et al., Effect of Pigment Packaging on Diffuse Reflectance Spectroscopy of Samples Containing Red Blood Cells, Optics Letts., 29:9, May 1, 2004, pp. 965-967.
Georgakoudi, I., et al., "Trimodal Spectroscopy for the Detection and Characterization of Cervical Precancers In Vivo", Am. J. Obstet. Gynol., vol. 186, No. 3, Mar. 2002, pp. 374-382.
Gurjar, R., et al., "Imaging Human Epithelial Properties with Polarized Light Scattering Spectroscopy", Nature Medicine, vol. 7, No. 11, Nov. 2001, pp. 1245-1248.
Horwitz, J., et al., "Micro-Architectural Alterations in Endoscopically Normal Mucosa Provides Accurate Risk Stratification for Colorectal Neoplasma", AJG Abstracts, vol. 99, No. 10, Undated, p. S326.
Jacques, S., et al., "Imaging Superficial Tissues with Polarized Light", Lasers in Surgery and Medicine, vol. 26, 2000, pp. 199-129.
Kim, Y.L., et al., "Simultaneous Measurement of Angular and Spectral Properties of Light Scattering for Characterization of Tissue Microarchitecture and its Alteration in Early Precancer", IEEE Xplore Abstract, Jan. 23, 2009 (downloaded), published Oct. 27, 2003, 1 page.
Lin, Wei Chiang, et al., "Intraoperative Application of Optical Spectroscopy in the Presence of Blood", IEEE J. on Selected Topics in Quantum Electronics, vol. 7, No. 6, Nov./Dec. 2001, pp. 996-1003.
Liu, Y, et al. "Light scattering 'fingerprinting' for characterization of smooth muscle cell proliferation" Advanced Biomedical and Clinical Diagnostic Systems II. Edited by Cohn, Gerald E., et al. Proceedings of the SPIE, vol. 5319, pp. 32-40 (2004).
McDonald, D., et al., "Imaging of Angiogenesis: From Microscope to Clinic", Nature Medicine: Angiogenesis Focus, vol. 9, No. 6, Jun. 2003, pp. 713-725.
Mourant, J.R., et al., "Predications and Measurements of Scattering and Absorption Over Broad Wavelength Ranges in Tissue Phantoms", Applied Optics, vol. 36, No. 4, Feb. 1, 1997. pp. 949-957.
Muller, M.G., et al., "Spectroscopic Detection and Evaluation of Morphologic and Biochemical Changes in Early Human Oral Carcinoma", American Cancer Society, 2003, pp. 1681-1692.
Roy, Hemant K., "Down-regulation of SNAIL Supresses MIN Mouse Tumorigenesis", Mol. Cancer Ter., vol. 3, No. 9, Sep. 2004, pp. 1159-1165.
Roy, Hemant K. et al., "Spectral markers in Preneoplastic Intestinal Mucosa", Cancer Epidermol Biomarkers Pre, vol. 14, No. 7, Jul. 2005, pp. 1639-1645.
Roy, Hemant K., et al., "Four Dimensional Elastic Light Scattering Fingerprints as Preneoplastic Markers in the Rat Model of Colon Carcinogenesis", Gastroenterology, 2004, vol. 126, pp. 1071-1081.
Wali, R.K., et al., "Increased Microvascular Blood Content is an Early Event in Colon Carcinogenesis", downloaded from gut.bmj-journals.com on Apr. 21, 2005, pp. 654-660.
Zonios, George, et al., Diffuse Reflectance Spectroscopy of Human Adenomatous Colon Polyps In Vivo, Applied Optics, vol. 38, No. 31, Nov. 1, 1999, pp. 6628-6637.
International Search Report issued Jan. 29, 2008 in corresponding PCT/US2007/12359.
Jan. 15, 2014 Office Action issued in U.S. Appl. No. 11/261,452.
Feb. 17, 2014 Supplementary Search Report issued in European Patent Application No. 10 72 9601.
Jul. 24, 2012 Office Action issued in Japanese Patent Application No. 2009-512139 (with translation).
Feb. 25, 2014 Office Action issued in Japanese Patent Application No. 2012-235160 (with translation).

\* cited by examiner

US 9,314,164 B2

METHOD OF USING THE DETECTION OF EARLY INCREASE IN MICROVASCULAR BLOOD CONTENT TO DISTINGUISH BETWEEN ADENOMATOUS AND HYPERPLASTIC POLYPS

PRIORITY CLAIM

This application is a continuation in part of and claims priority to U.S. application Ser. No. 11/604,653 entitled "Method of Recognizing Abnormal Tissue Using the Detection of Early Increase in Microvascular Blood Content," which was filed on Nov. 27, 2006 and the applications to which it claims priority, U.S. Application No. 60/801,947 entitled "Guide-To-Colonoscopy By Optical Detection Of Colonic Micro-Circulation And Applications Of Same," which was filed on May 19, 2006, the contents of which are expressly incorporated by reference herein. This application is also a continuation-in-part and claims priority to co-pending U.S. patent application Ser. No. 11/261,452 entitled "Multi-Dimensional Elastic Light Scattering," filed Oct. 27, 2005, with the same assignee as the prevent invention, the disclosure of which is incorporated in its entirety herein by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

STATEMENT AS TO RIGHTS UNDER FEDERALLY-SPONSORED RESEARCH

This invention was made with government support under Grant No. R01CA109861 awarded by National Institutes of Health of the United States. The government has certain rights in the invention.

FIELD OF THE INVENTION

The present inventions relate generally to light scattering and absorption, and in particular to methods of distinguishing between possible adenomatous and benign (hyperplastic) polyps using a detected early increase in microvascular blood supply and corresponding applications including in vivo tumor imaging, screening, detecting and treatment, and, in particular, "Early Increase in microvascular Blood Supply" (EIBS) that exists in tissues that are close to, but are not themselves, the lesion or tumor and in tissues that precede the development of such lesions or tumors.

BACKGROUND OF THE INVENTION

There are various techniques known for determining abnormality in tissues. Of these techniques, those that are most relevant to the present invention are techniques in which there is detected an increase in blood within tissue that is abnormal. While such techniques have advantages in and of themselves as compared to other methods, they require testing of the abnormal tissue itself, which may be difficult to detect. Further, such methods are usable only after the abnormality is sufficiently large, such as a cancerous tissue.

Accordingly, the present invention provides a variety of advantageous optical techniques for assisting in the distinguishing between possible adenomatous and hyperplastic polyps, particularly using optical measurements, early in the development of the abnormal tissues themselves.

SUMMARY OF THE INVENTION

The present invention, in one aspect, relates to a method for distinguishing between possible adenomatous and hyperplastic polyps using what is referred to as "Early Increase in microvascular Blood Supply" (EIBS) that exists in tissues that are close to, but are not themselves, the abnormal tissue.

A particular application described herein is for detection of such lesions in colonic mucosa in early colorectal cancer, but other applications are described as well.

In one aspect, the present invention describes a method of providing an indication that a polyp is a possible adenomatous polyp or a hyperplastic polyp by identifying tissue of the organ that contains microvasulature therein, wherein the tissue does not contain the living tissue that may be abnormal and determining from the blood content within the microvasculature whether an early increase in microvascular blood supply exists in the tissue to indicate whether the polyp is the possible adenomatous polyp or the hyperplastic polyp.

In another aspect, the present invention provides a method of providing an indication that a polyp is one of a possible adenomatous polyp and a hyperplastic polyp comprising the steps of:

inserting an illumination probe such that a light source within the illumination probe is disposed in a location that is at a surface of the organ that contains the polyp;

illuminating microvasculature within a tissue of the organ around the polyp;

detecting scattered light that results from the step of illuminating the location, wherein the detected light is obtained substantially from light scattered from blood in the microvasculature that is within the tissue of the organ that does not contain the polyp;

estimating at least one of blood content and blood flow in the microvasculature using the detected light; and identifying that the polyp is one of the possible adenomatous polyp and the hyperplastic polyp using the at least one of estimated blood content and blood flow.

BRIEF DESCRIPTION OF THE DRAWINGS

These and other aspects and features of the present inventions will become apparent to those of ordinary skill in the art upon review of the following description of specific embodiments of the invention in conjunction with the accompanying figures, wherein.

DETAILED DESCRIPTION OF THE EMBODIMENTS

Figure 1:
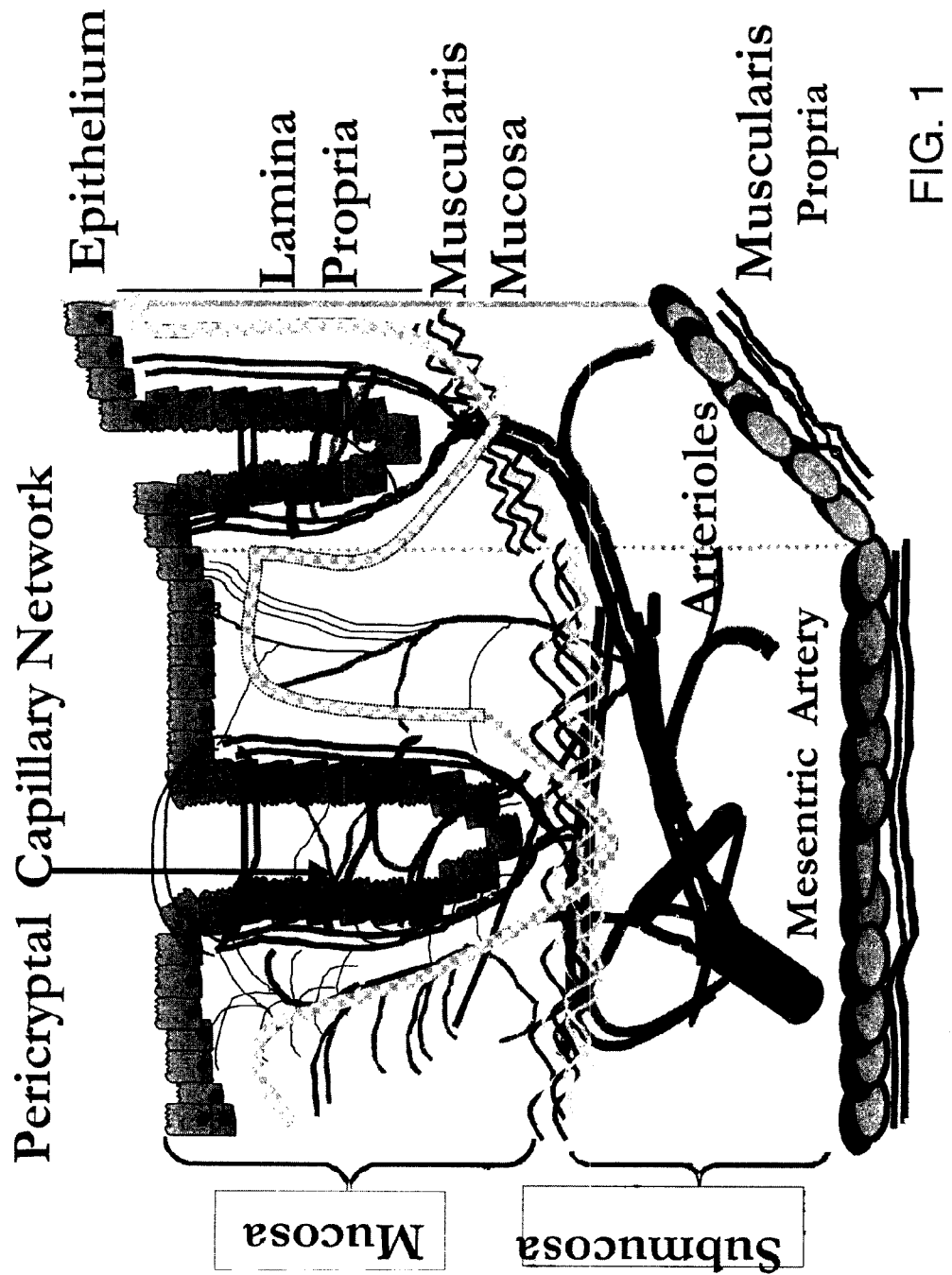
FIG. 1 illustrates organization of blood supply in colonic mucosa and submucosa.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, not is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The present invention, in one aspect, relates to methods for examining a target for tumors or lesions using what is referred to as "Early Increase in microvascular Blood Supply" (EIBS) that exists in tissues that are close to, but are not themselves, the lesion or tumor. While the abnormal tissue can be a lesion or tumor, the abnormal tissue can also be tissue that precedes formation of a lesion or tumor, such as a precancerous adenoma, aberrant crypt foci, tissues that precede the development of dysplastic lesions that themselves do not yet exhibit dysplastic phenotype, and tissues in the vicinity of these lesions or pre-dysplastic tissues.

A particular application described herein is for detection of such lesions in colonic mucosa in early colorectal cancer ("CRC"), but other applications are described as well.

The target is a sample related to a living subject such as a human being or animal. The sample is a part of the living subject such that the sample is a biological sample, wherein the biological sample may have tissue developing a cancerous disease.

The neoplastic disease is a process that leads to a tumor or lesion, wherein the tumor or lesion is an abnormal living tissue (either premalignant or cancerous), such as pancreatic cancer, a colon cancer, an adenomatous polyp of the colon, a liver cancer, a lung cancer, a breast cancer, or other cancers.

The measuring step is preferably performed in vivo, though it can be performed ex vivo as well. The measuring step may further comprise the step of acquiring an image of the target. The image, obtained at the time of detection, can be used to later analyze the extent of the tumor, as well as its location. Measuring of blood content using interacted light, which can include scattering as well as other optical methods, can include insertion of a probe for in-vivo usages in which blood content and/or flow is measured in tissue of a solid organ. Also, the present invention can be used to insert a probe into a body cavity, such as for measurements of tissues that are in the GI tract, respiratory track, or the like.

In one embodiment, the method comprises projecting a beam of light to a target that has tissues with blood circulation therein. At least one spectrum of light scattered from the target is then measured, and blood supply information related to the target is obtained from the measured at least one spectrum. The obtained blood supply information comprises data related to at least one of blood content, blood oxygenation, blood flow and blood volume.

The method according to an embodiment of the invention may include obtaining a first set of the blood supply information from a first location of the target and then obtaining a second set of the blood supply information from a second location of the target. The first set of the blood supply information at a first location of the target and the second set of the blood supply information at a second location of the target can then be compared to determine the status of the target. One can compare the data to indicate whether the tumor or lesion exists at all by comparison to previously established microvascular blood content values from patients who harbor neoplasia and from those who are neoplasia free. The data can also indicate whether the tumor or lesion is closer the first or second location by comparison of the blood content values from the first and second locations. Rather than measuring blood content in a given tissue site, at least two but preferably more tissue sites may be assessed located within a given area of tissue and the statistical properties of blood content or blood flow distribution can be determined for this area to determine the status of the target. For example, the maximal blood content within an area can be used to determine the status of the target. Other statistical measures include mean, average, median, standard deviation, maximal value, and minimal value.

Rather than having different locations, the same location can be compared at different times, days, months or years apart, to determine the status of the target, and in particular whether the tumor or lesion has developed or if it previously existed whether it has gotten larger.

The present invention, in another aspect, relates to an apparatus for examining a target. In one embodiment, the apparatus comprises a light source configured and positioned to project a beam of light to a target; and means for measuring at least one spectrum of light scattered from the target; and means for obtaining blood supply information related to the target from the measured at least one spectrum.

The apparatus may further comprise a detector that obtains a first set of the blood supply information at a first location of the target. The same detector can be used to obtain a second set of the blood supply information at a second location of the target. An algorithm, which is executed by a controller or computer, analyzes that data is used to determine the status of the target, typically by comparing the first set of the blood supply information at a first location of the target and the second set of the blood supply information at a second location, although comparisons against reference blood supply information (that does or does not suggest the presence of a tumor or lesion) can be used as well. This same apparatus can be used to implement the method mentioned above where the same location is sampled at different points in time.

A superficial and subsuperficial polarization and spectral data analysis algorithm that allows for discrimination between spectral data obtained from the mucosal and the submucosal tissue is described in the following Equation 1. It is noted that this algorithm, because it is based on the quantitative analysis of spectroscopic signals recorded as a result of elastic scattering and absorption of light in tissue without the need for tissue biopsy or any other preparation, allows for almost real-time processing of the polarization gated signals, which makes it very useful for clinical screening applications.

Polarization gating enables assessment of blood content in several tissue compartments at the same time. The two principal tissue compartments that are being analyzed for the blood content are the "superficial" (e.g. mucosal) and "subsuperficial" (e.g. mucosal and submucosal) tissues (FIG. 1). In order to assess blood content and/or blood flow in superficial tissue, polarization-gated spectrum is preferably used. Blood content in subsuperficial tissue can be measured by using co-polarized spectrum, arbitrarily polarized (also referred to as unpolarized or total) spectrum (which is the sum of co-polarized and cross-polarized signals), or cross-polarized spectrum. These three signals have progressively deeper depths of penetrations. The depth of penetration of these signals can be selected by the instrumentation design in order to selectively probe mucosal and mucosal/submucosal tissue for a given organ and tissue type. The polarization-gated signal $S(\lambda)$ is taken as the difference between copolarized and crosspolarized signals, each normalized by the corresponding copolarized and crosspolarized spectra from a polytetrafluoroethylene reflectance standard (Ocean Optics). Co-polarized, arbitrarily polarized (also known as unpolarized) and cross-polarized signals ($D(\lambda)$) are normalized accordingly. In the teachings that follow, as an example, it is considered that subsuperficial blood content is measured from the cross-polarized signal. It should be understood, however, that similar analysis can be performed based on co-polarized and arbitrarily polarized signals. Thus, in principle, blood content can be measured for four different depths of penetration.

In both cases of superficial and subsuperficial blood content, it is assumed that the variability in path length due to differences in optical properties within the sample is small. While it is known that Beer's law cannot be directly applied to the analysis of scattered light because of unknown attenuation due to scattering, Beer's law served as the starting point for the analysis, as attenuation due to absorption has an inverse exponential relationship with absorber concentration. This assumption can be expressed as follows:

$$S(\lambda) = S_{scattering}(\lambda) \exp[-L_S(\alpha_{HbO2} A^{HbO2}(\lambda) + \alpha_{Hb} A^{Hb}(\lambda))]$$

$$D(\lambda) = S_{scattering}(\lambda) \exp[-L_D(\beta_{HbO2} A^{HbO2}(\lambda) + \beta_{Hb} A^{Hb}(\lambda))], \quad (1)$$

where $S_{scattering}(\lambda)$ and $D_{scattering}(\lambda)$ represent light scattering signals from the superficial and subsuperficial layers of a sample, respectively, if it were devoid of absorbers. $A(\lambda)$ represents the absorption spectrum of all of the absorbers present (oxygenated and deoxygenated hemoglobin), coefficients $L_S$ and $L_D$ represent the path lengths for polarization-gated and cross-polarized signals, and coefficients $\alpha$ and $\beta$ represent the absorbers' concentrations for superficial and subsuperficial tissue depths. To account for different contributions of oxygenated and deoxygenated hemoglobin, two coefficients are used: $\alpha_{HbO2}$ and $\alpha_{Hb}$ in case of superficial blood content and $\beta_{HbO2}$ and $\beta_{Hb}$ in case of subsuperficial blood content. Similar analysis can be performed for co-polarized and arbitrarily polarized (i.e., total, unpolarized) spectra.

Spectra for deoxygenated and oxygenated blood content can be measured in a hemoglobin solution in water. The solution is placed in a glass-bottomed culture slide directly on top of a reflectance standard and measured to obtain a spectrum $A^{HbO2}(\lambda)$. It is then deoxygenated by adding sodium dithionite to measure the $A^{Hb}(\lambda)$. $L_S$ and $L_D$ are determined in the process of initial instrument calibration in tissue models. The remaining unknowns for the analysis are $S_{scattering}(\lambda)$ and $D_{scattering}(\lambda)$. To fill this gap it is assumed that expected $S_{scattering}(\lambda)$ and $D_{scattering}(\lambda)$ should have a smooth decreasing spectral line shape between $\lambda=480$ and 680 nm, thereby lacking spectral features of hemoglobin absorption, which include absorption bands at 542 and 576 nm in the case of oxygenated blood and 555 nm in the case of deoxygenated blood. In particular, second-order decreasing polynomial or inverse power-law spectral line shapes can be used as target line shapes with essentially the same results. Over this narrow spectral range, this assumption is reasonable. Thus the superficial and subsuperficial polarization and spectral data analysis algorithm tests values of $\alpha_{HbO2}$ and $\alpha_{Hb}$ for superficial and $\beta_{HbO2}$ and $\beta_{Hb}$ for subsuperficial tissue over the range of interest and finds those that provide the best agreement between the resulting $S_{scattering}(\lambda)$ and $D_{scattering}(\lambda)$ and a target line shape in the least-squares sense. This process can be continued iteratively.

Once coefficients $\alpha_{HbO2}$ and $\alpha_{Hb}$ are found, a number of other related metrics characterizing blood content can be found including total blood content=$\alpha_{HbO2}+\alpha_{Hb}$ and oxygen saturation=$\alpha_{HbO2}/(\alpha_{HbO2}+\alpha_{Hb})$. (2)

The validity of all equations was verified using tissue phantom experiments.

In one embodiment, at least one spectrum of light scattered from the target is measured by a fiber optic probe, wherein the fiber optic probe comprises a polarization-gated fiber optic probe configured to detect the blood supply information. The light source comprises an incoherent light source (such as a xenon lamp).

In one embodiment, the fiber optic probe includes a proximal end portion, an opposite, distal portion, and a body portion with a longitudinal axis defined between the proximal end portion and the distal portion. The body portion is formed with a cavity along the longitudinal axis. At least one first type of fiber is used for delivering a beam of energy to a target, wherein the at least one first type fiber is at least partially positioned within the cavity of the body portion. An optical element is positioned at the proximal end portion and configured to focus the beam of energy to the target. At least one second type fiber is used for collecting scattered energy from the target, wherein the at least one second type fiber is at least partially positioned within the cavity of the body portion.

The fiber optic probe may further comprise at least one linear polarizer optically coupled to the at least one first type fiber and the at least one second type fiber and positioned proximate to the proximal end portion, and wherein the optical element is positioned at the proximal end portion and configured to focus the scattered energy from the target to the at least one linear polarizes for the at least one second type fiber to collect.

The optical element comprises at least one of a ball lens, a graded refractive index lens, an aspheric lens, cylindrical lens, convex-convex lens, and plano-convex lens, although preferably just a single lens is used. Lenses or any combinations of them other than these above-mentioned lenses can also be used. It is further noted that different lenses can be used to assist in discriminating measurements and to achieve different tissue penetration depths. Thus, for example, to achieve the shortest penetration depth, a lens can be positioned at the focal distance from the end of the light-collecting fibers with the fibers positioned symmetrically around the axis of the lens. This configuration further increases the intensity of collected light, particularly when a probe is at a distance form tissue, and provides improved stability of the signals collected by the probe in terms of different distances from tissue (if a probe is not in contact with tissue) and pressures exerted by the probe onto tissue (if a probe is in contact with tissue). Shorter penetration depth can also be achieved by using a lens with a shorter focal distance, smaller numerical aperture of the illumination and/or collection fibers, and larger distance between illumination and collection fiber. In principle, penetration depths from a few tens of microns to a few millimeters can be achieved by choosing a proper combination of these probe characteristics.

The at least one first type fiber comprises an illumination fiber, wherein the illumination fiber is optically coupled to the light source.

The at least one second type fiber can also be formed with one or more collection fibers, wherein the one or more collection fibers are optically coupled to an imaging spectrograph and a CCD at the distal end portion, which imaging spectrograph is used to obtain an image of the target. The body portion comprises a tubing.

The following further details of the preferred embodiments, will further describe the invention. As will become apparent, a substantial part of the following disclosure relates to the EIBS phenomenon as applied to determination of the presence of colonic neoplasia (adenomatous polyp or carcinoma) through analysis of colonic tissue remote to the lesion and as a guide to the determination of the location of a tumor or lesion with the colon. This disclosure is also applicable to detection of tumors or lesions within other organs, and to the extent variations exist with respect to such detection in different organs, such is noted.

Although it has been well established that blood supply to tumor tissue is increased, very little attention has been given to alterations in blood supply at the pre-neoplastic stage and histologically/endoscopically normal appearing mucosa outside the extend of a neoplastic or pre-neoplastic lesion, largely due to the methodological difficulties in reliably quantitating microvascular blood supply. EIBS is most pronounced in the very superficial mucosa (peri-cryptal capillary plexus). This makes up a very small amount of total colonic microcirculation. The reason polarization-gated optical spectroscopy can detect this is that it can specifically and accurately analyze this plexus.

It is further noted that the present invention can distinguish between benign and malignant tumors, such that when a tumor is seen, looking at the surrounding normal mucosa can assist in distinguishing a hyperplastic (benign) from an adenomatous (premalignant) tumor. Abnormal blood supply in the microscopically normal mucosa adjacent to the lesion—EIBS—will be seen in adenomatous but not hyperplastic polyps. Furthermore, previous angiogenesis studies focused on blood supply increase to a neoplastic lesion itself. EIBS manifests itself as an increase in blood supply in the microcirculation (primarily mucosa) supplying blood to epithelium. EIBS occurs very early during the process of colon carcinogenesis. Our data in animal models of colon carcinogenesis showed that EIBS starts at earlier than development of adenomas and aberrant crypt foci (i.e. the earliest marker of carcinogenesis) and precedes the development of currently known molecular markers of colonic neoplasia. Furthermore, EIBS can be detected outside a neoplastic lesion. This allows for detecting a lesion outside its physical extent, as discussed by the examples and further disclosure provided below.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Figure 2:
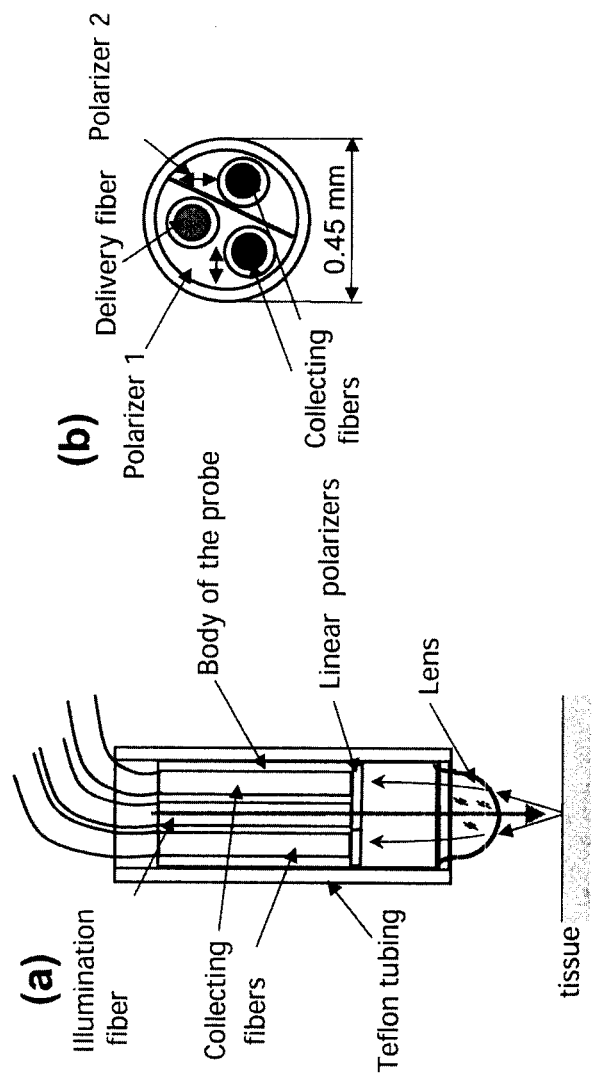
FIG. 2 shows schematically according to one embodiment of the present invention a fiber-optic polarization-gated probe: (a) side view and (b) distal (i.e., close to tissue surface) tip.
Figure 3:
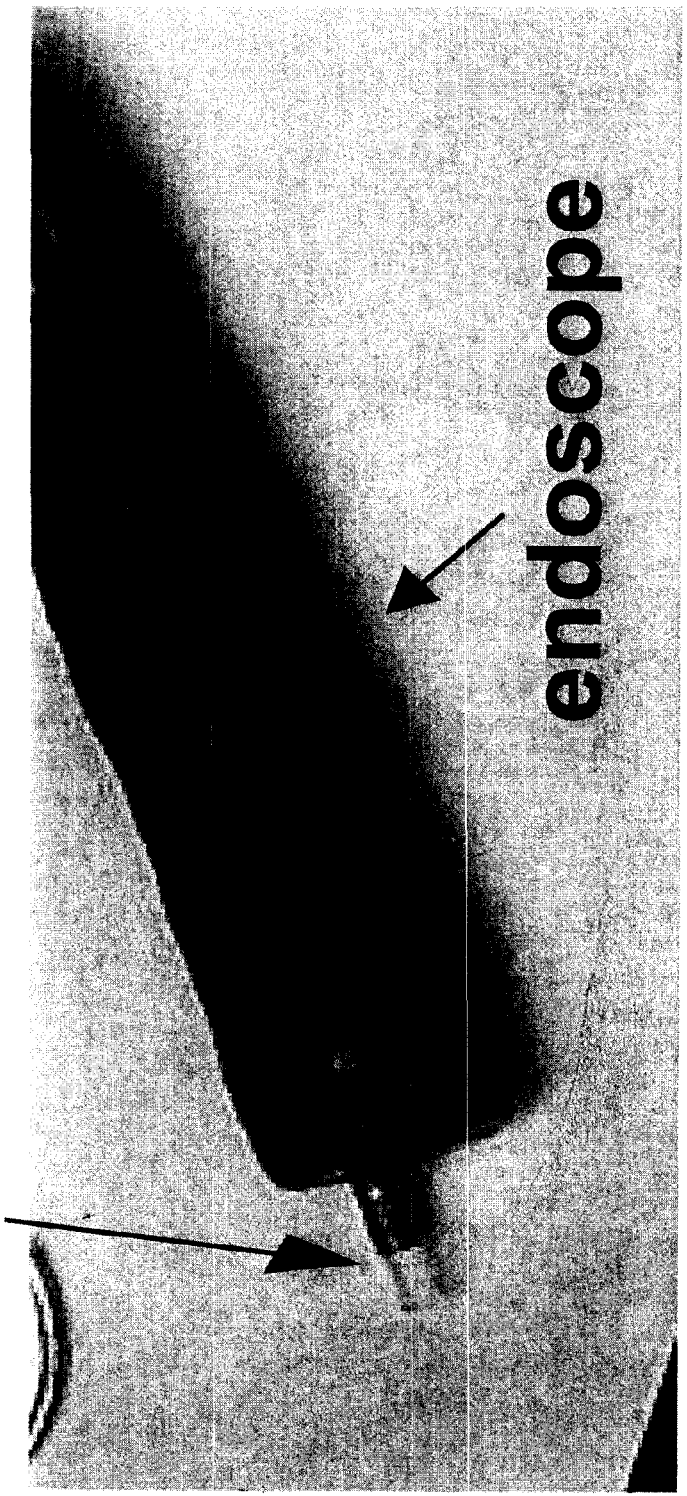
FIG. 3 shows according to one embodiment of the present invention photographically a polarization-gated probe in an accessory channel of an endoscope.

Polarization Gated Fiber-Optic Probe to Detect EIBS:

In one aspect, a fiber-optic probe has been developed to accurately detect blood supply in tissue mucosa. FIG. 2 illustrates the design of the probe in one embodiment and FIG. 3 shows a photograph of the probe protruding from an accessory channel of a colonoscope. The probe has one or more 100 μm-diameter fibers, one of which was used for delivery of linearly polarized light from a Xe-lamp onto tissue surface and the other two fibers were for collecting scattered light from the tissue. A positive aspherical lens was positioned at the focal distance from the fiber tips. Several lens types were also tested, including ball, graded refractive index (GRIN), and aspherical lenses. All of the different types of lenses could be used and these provide different performance of the probe in terms of the depth of penetration. In the configuration where the lens was positioned at the focal distance from the fiber tips, it focused light backscattered from a sample onto different fibers depending on the angle of backscattering. It also ensured that all collection fibers receive scattered light from the same tissue site, which also coincides with the illumination spot. The lens does not have to be positioned at the focal distance from the fibers, but this configuration provides better performance in terms of 1) shorter penetration depth, in particularly for the polarization gated signal, 2) increases signal level and, thus, time required to collect the signal with sufficient signal-to-noise ratio, 3) prevents collection of specular reflection from probe and tissue surfaces, and 4) improves stability of the measurements in terms of probe displacement from tissue surface in non-contact geometry or the pressure exerted by the probe onto a sample. In the proximal end of the probe, the linear array of fibers was coupled to an imaging spectrograph and a CCD. Two thin film polarizer's were mounted on the proximal tip of the probe to polarize the incident light and enable collection of both polarization components (i.e. parallel $I \parallel$ and $I^\perp$ perpendicular to the incident polarization) of the backscattered light to allow for polarization gating. All components of the probe were made from FDA approved materials.

A lens at the probe tip allows selecting a desired penetration depth. For example, to achieve a shorter penetration depth, a lens can be positioned at the focal distance from the end of the fibers with the fibers positioned symmetrically around the axis of the lens. Furthermore, one can use a lens with a shorter focal distance, smaller numerical aperture of the illumination and/or collection fibers, and a larger distance between the illumination and collection fiber. For example, probes were fabricated with a GRIN lens with the penetration depth in colon tissue for polarization-gated signal ~85 microns (~1.7 mean free path lengths) and that for cross-polarized light ~260 microns. A ball lens probe with penetration depths ~23 and 275 microns was also developed. As such, it is apparent that penetration depths from a few tens of microns to a few millimeters can be achieved by choosing a proper combination of these probe characteristics.

Polarization Gating:

Polarization gating has been previously used to selectively record short-traveling photons as well as to increase contrast for photons emerging from deeper tissue. As has been shown by our group, the differential polarization signal $\Delta I(\lambda) = I \parallel (\lambda) - I^\perp(\lambda)$ is primarily contributed by scatterers located close to the tissue surface and, therefore, particularly sensitive to the properties of the superficial tissues, e. g. epithelial. Our experiments showed that the contribution to the differential polarization signal from deeper tissue structures decreases exponentially with "optical distance" to the structure and, hence, with depth ($\tau = L/ls$ with L "physical" depth and ls photon mean free path length in tissue). Because optical density of epithelium is much smaller than that of underlying connective tissue, in the colon, differential polarization signals are primarily collected from the epithelium plus up to ~50 μm of underlying connective tissue. This near-surface portion of subepithelial stoma contains a network of capillaries supplying oxygen to the epithelium. Co-polarized signal I $\parallel$, arbitrarily polarized signal $I \parallel + I^\perp$ and cross-polarized signal $I^\perp$ contain information about progressively deeper tissue, up to several millimeters below the surface for certain probe configurations.

Measurement of Superficial Blood Content:

The blood content in the capillaries immediately below epithelium can be quantitatively estimated from the spectral analysis of $\Delta I(\lambda)$. We developed several methods of spectral data analysis. The following example [Eq. 3] discusses an earlier version of the method that provides for analysis of superficial blood content. A more recent version [Eqs. 1 & 2] that provides improved accuracy of blood content estimation in both the superficial and subsuperficial mucosa is discussed above.

With respect to this earlier version, it operates based on a determination of blood content values that include effects of both scattering and absorption by red blood cells in the microvasculature and model the presence of absorption bands in the spectra due to both light absorption and scattering by blood.

We obtained the scattering images of rats' red blood cells (RBCs). Although Hb primarily absorbs visible light, it is not sufficient to measure only the absorption spectra of Hb molecules. RBCs, which are filled with Hb, are large scatterers approximately 7-8 microns in diameter. Therefore, the contribution from the RBCs couples both absorption and scattering. Our data demonstrate that differential polarization signal measured from a tissue $\Delta I(\lambda)$ can be written as $$\Delta I(\lambda) = \Delta Is(\lambda) + \alpha \Delta I_{RBC}, \quad (3)$$

where $\Delta Is(\lambda)$ is the signal contributed by epithelial cells and other non-RBC components of the superficial tissue (not a priori known), $\Delta I_{RBC}$ is the signal experimentally measured from isolated ref blood cells (thus, this signal is known), and a is the number density of RBCs per $mm^2$. This early version of the polarization and spectral data analysis algorithm for superficial blood content was used to find the fitting parameter α by minimizing the Hb absorption bands in $\Delta Is(\lambda)$. This early version of the polarization and spectral data analysis algorithm, rather than using an exponential attenuation of light propagating in tissue by the tissue blood content that was used in Eq. 1, relies upon a linear calculation where the contribution from the red blood cells is assumed to be additive to that of tissue scattering; this contribution includes both light absorption and red blood cell scattering.

For in situ applications, where hemoglobin is present in bot oxygenated ($\Delta I_{RBC-O2}(\lambda)$), and deoxygenated ($I_{RBC-O2}(\lambda)$) forms, $$\Delta I_{RBC}(\chi;\lambda) = \chi \Delta I_{RBC-O2}(\lambda) + (1-\chi) I_{RBC-O2}(\lambda) \quad (4)$$

With χ the oxygen saturation coefficient also determined by means of optimization.

Measurement of Subsuperficial Blood Content.

We also assessed blood supply in the deeper tissue layers, i.e. mucosa and submucosa, via $I^{\perp}(\lambda)$ (as opposed to $\Delta I$, this signal is primarily contributed not by single but multiple scattering process). For subsuperficial blood content, we developed several methods of spectral data analysis. The following example in Eq. 5 discusses an earlier version of the method. A more recent version that provides improved accuracy of blood content estimation is discussed above in Eqs. 1 & 2.

The changes in the blood supply to mucosa/submucosa is detected, as noted, by means of the analysis of the cross-polarized signal $I^{\perp}(\lambda)$. Briefly, a diffusion approximation model is fit to the data. The model $I_M$ depends on the spectra of the transport scattering $\mu'_s(\lambda)$ and absorption coefficient $$\mu_\alpha(\lambda) = \chi \mu_{\alpha-O2}(\lambda) + (1-\chi)\mu_{\alpha-DO2}(\lambda), \quad (5)$$

which is contributed by both oxygenated $\mu_{\alpha-O2}$ and deoxygenated $\mu_{\alpha-DO2}$ Hb species with oxygen saturation $\chi$ found as a fitting parameter $\mu_\alpha$ is proportional to the concentration of the respective form of Hb in tissue. It is conventionally assumed that Hb is the only significant absorber of visible light in the mucosa and $\mu'_s(\lambda)$ should not exhibit Hb absorption bands.

This diffusion approximation-based, early version of the algorithm requires substantial processing time (on the order of several minutes per sample), rather than the nearly real-time results from the algorithm of Eq. 1 discussed above. The reason for such an improvement is because the algorithm of Eq. 1 does not require the use of a diffusion approximation that is computationally intensive.

Measurement of Oxygen Saturation.

As discussed above, due to distinctly different absorption spectra of oxy- and deoxy-hemoglobin, not only does spectral analysis of polarization gated signals enable measurement of blood content but also blood oxygenation (aka. oxygen saturation, $S_{O2}=\chi$. We validated $S_{O2}$ calculations from spectral data. The accuracy of oxygen saturation measurement was excellent with error <1%.

Accuracy of EIBS Assessment Using Fiber-Optic Probe.

Figure 4:
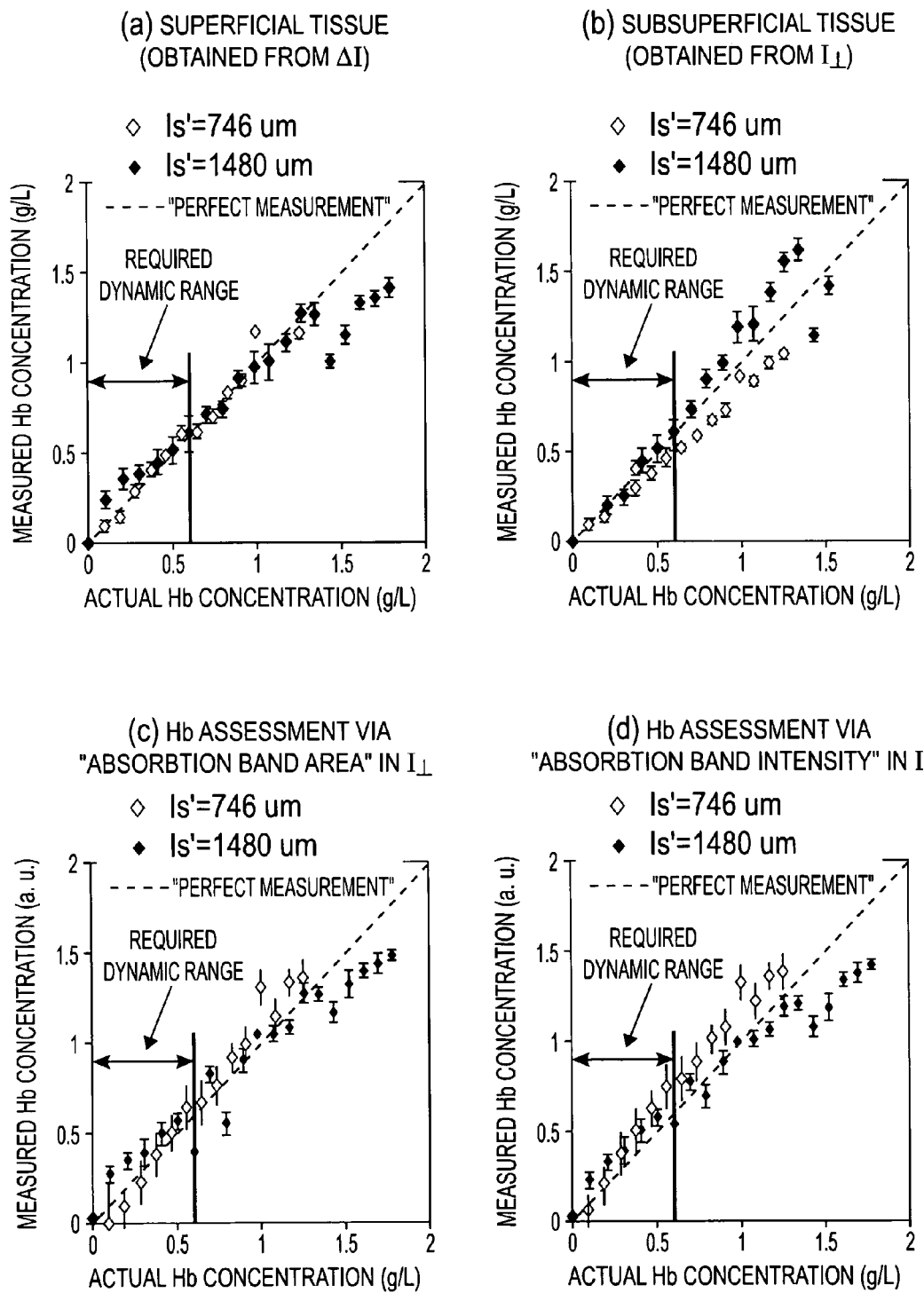
FIG. 4 shows according to one embodiment of the present invention accuracy of optical measurement of Hb content in (a) superficial tissue (obtained from $\Delta I(k)$ using Eq. 1) and in (b-d) subsuperficial tissue obtained using Equation (1) (panel (a)) and alternate methods: absorption band area (panel (b)) and absorption band intensity (pane (c)). Is' stands for transport mean free path length. The dashed line shows what the data would look like if the accuracy of measurements were 100%.

We also validated the ability of the probe to assess hemoglobin concentration in studies with tissue models. The tissue models were fabricated and the analysis of spectral data was performed as discussed above. As shown in FIG. 4, the probe enables accurate assessment of hemoglobin concentration. The standard error of measurements for concentrations <12 g/L for superficial tissue was <0.01 g/L and that for deeper tissue was <0.02 g/L. We point out that according to EIBS data in animals as well as humans, the dynamic range of Hb concentrations was well within this range. Thus, the probe provides sufficiently accurate measurement of blood content in physiologic range with error of measurement sufficient to reliably identify EIBS.

It is also possible to measure blood content based on the analysis of the area of hemoglobin absorption spectral band and/or the maximum of this absorption band. As shown in FIGS. 4(c, d), both "absorption band area" and "absorption band intensity" methods enable accurate assessment of hemoglobin concentration with the 10 error of measurements for concentrations <1.2 g/L, 0.02 g/L and 0.03 g/L, respectively, and for concentrations from 1.2 to 18 g/L, 0.07 g/L and 0.09 g/L, respectively.

EIBS Precedes Formation of Known Markers of Colon Carcinogenesis.

Figure 5:
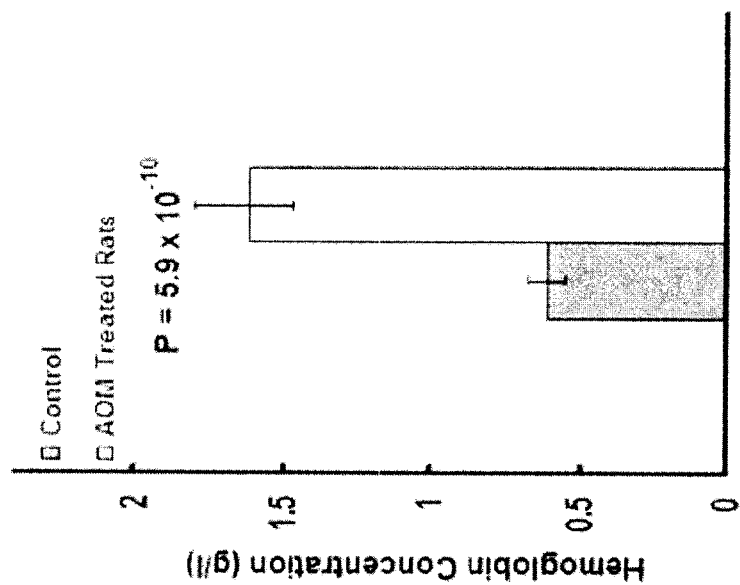
FIG. 5 shows alterations of blood supply in early experimental carcinogenesis observed using polarization-gated signal according to one embodiment of the present invention. The shows EIBS in histologically normal mucosa (i.e., superficial tissue compartment) of AOM-treated rats two weeks after initiation of carcinogenesis by means of AOM injection. This early time point precedes the development of adenomas, aberrant crypt foci and any other currently known markers of colon carcinogenesis. EIBS was observed only in the distal colon of AOM-treated rats and no blood content increase was found in the proximal colon, consistent with the fact that precancerous and cancerous lesions develop primarily in the distal colon in this model.

EIBS precedes the development of any currently known histologic or molecular markers of colon carcinogenesis. Specifically, we assessed blood content in the colons of rats treated with a colon specific carcinogen, azoxymethane (AOM). The AOM-treated rat model is one of the most robust and widely used animal models of CRC. As in humans, in this model, neoplasia progresses through a well-defined sequence of events with the exception that the time course of carcinogenesis in the AOM-treated rat model is much faster than the one in humans: the earliest detectable marker of carcinogenesis, ACF, develops in 4-12 weeks after AOM injection, adenomas are observed in 20-30 weeks, and carcinomas develop after 40 weeks. No histologic, molecular or genetic markers have been shown to allow earlier diagnosis (<4-12 weeks). As shown in FIG. 5, our data demonstrate that EIBS occurs as early as 2 weeks after AOM-injection (p-value<$10^{-9}$). Importantly, EMS was detected only in the distal colon and not in the proximal colon (p-value<$10^{-11}$). This mirrors the progression of carcinogenesis in the AOM-treated rat model as AOM induces carcinogenesis primarily in the distal colon with only minimal effect on the proximal colon, as has been validated by numerous studies and our data as well.

EIBS is an Accurate Predictor of Colonic Neoplasia: Animal Study.

In order to assess whether EIBS may serve as a clinically useful biomarker, we determined the performance characteristics of EIBS to detect future ACF in AOM-treated rats. It was found that EIBS had excellent ability to distinguish animals at risk for CRC from the negative controls even at the pre-ACE stage of CRC, two weeks after AOM treatment. Indeed, the diagnostic accuracy of EIBS far exceeded conventional markers with high (>90%) sensitivity, specificity, positive and negative predictive values even at the earliest stages of colon carcinogenesis, preceding the development of currently known markers of CRC (Table 1).

TABLE 1

| EIBS diagnosis of predisposition to CRC in AOM-treated rat model | |
|---|---|
| Sensitivity | 94% |
| Specificity | 96% |
| PPV | 97% |
| NPV | 92% |

EIBS Gradient Localizes Adenomas: In Vivo Clinical Study.

To prove that EIBS and, importantly EIBS gradient (i.e., progressive increase in blood content towards an adenoma) can be observed in vivo. A pilot investigation was conducted in human subjects undergoing screening colonoscopies (196 patients including 48 with adenomas out of which 43 were diminutive and 5 advanced, 27 subjects with hyperplastic benign polyps, and 121 patients with negative colonoscopies). We used an endoscopically compatible fiber-optic probe discussed in the preceding section. The probe was inserted into the accessory channel of a colonoscope. During colonoscopy, EIBS spectral data were acquired by the probe from the following locations: adenomatous polyp (if present), an endoscopically normal location within 10 cm from the adenoma, from the same colonic segment where the adenoma was located (typically within 30 cm from the adenoma) and the other segments (dubbed "outside" segments).

In patients with negative colonoscopy, measurements were taken at random from each of the three colonic segments (i.e., descending colon including rectum and sigmoid colon, mid-transverse colon, and ascending colon including the cecum).

On average, three spectra were obtained from each tissue site and more than 10 different tissue sites were probed for each patient.

Figure 6A:
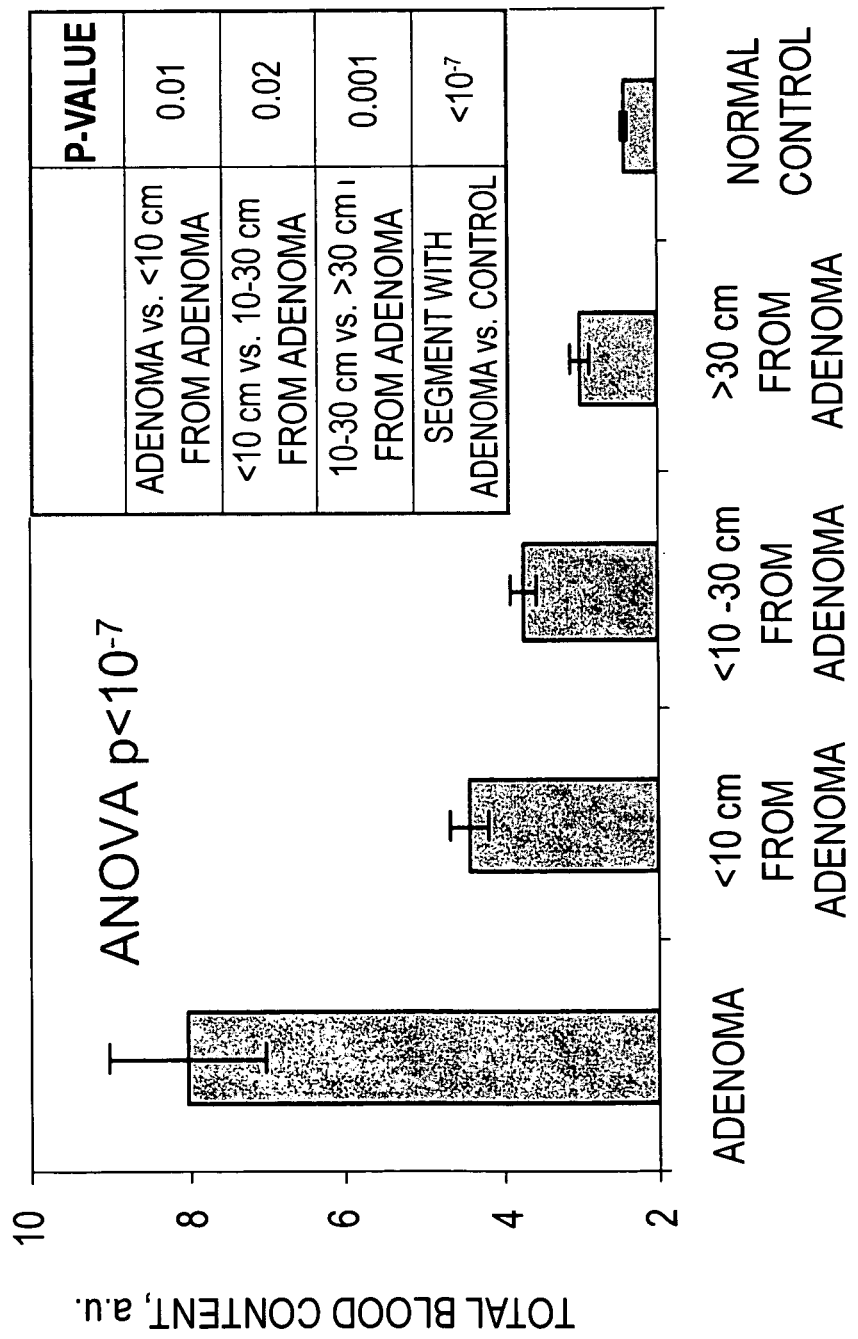
FIGS. 6(a)-6(d) show schematically according to one embodiment of the present invention the observation of EIBS in our in vivo studies (n=196 patients). The x-axis shows a location of EIBS reading in relation to the location of an adenoma. Normal control values were taken from patients with negative colonoscopy from the same colonic segments where adenomas were found in patients with positive colonoscopy. (a) EIBS from total blood content; (b) EIBS in superficial tissue (e.g. mucosa) extends >30 cm, i.e. EIBS can be observed in colonic segments other than the one where an adenoma is located; (c) EIBS in subsuperficial tissue (e.g. mucosa and superficial mucosa) extends <30 cm from the location of an adenoma; (d) Benign, hyperplastic polyps do not lead to EIBS outside extend of a polyp.
Figure 6B:
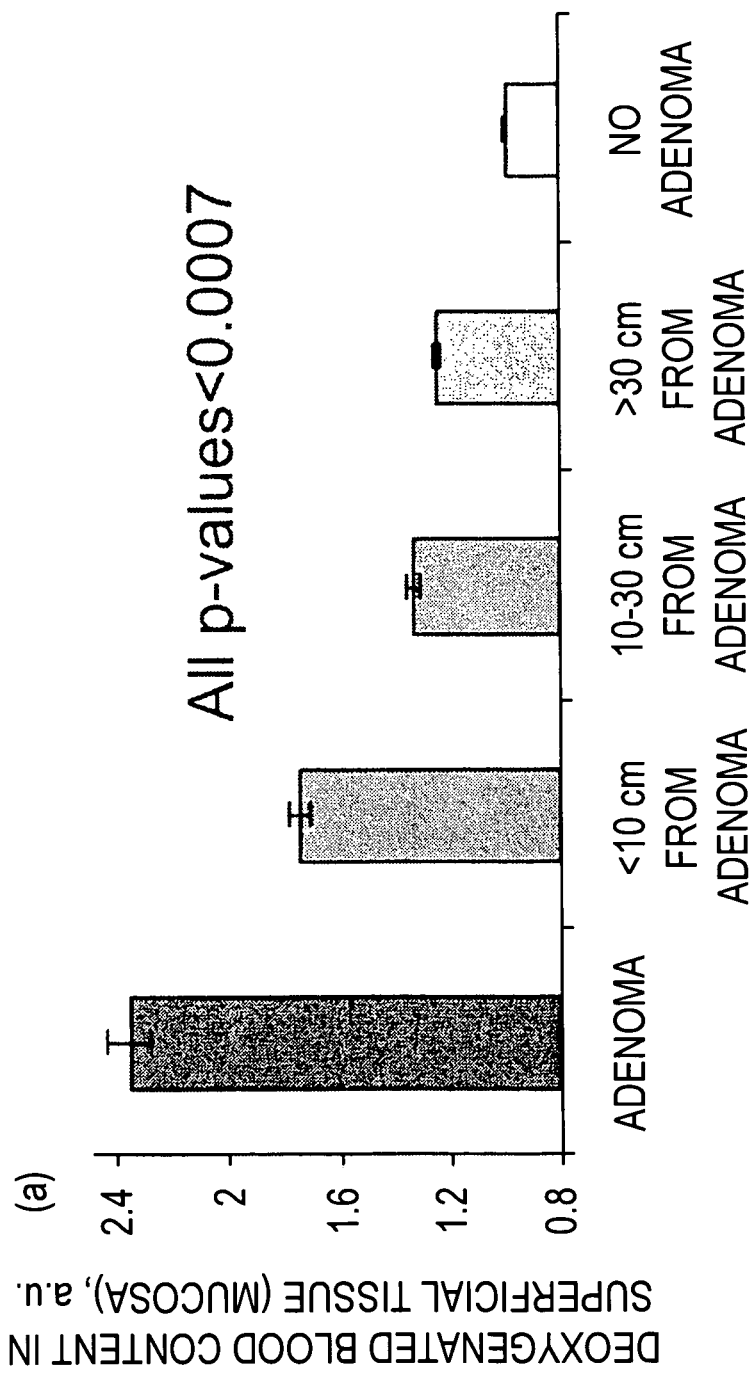
Figure 6C:
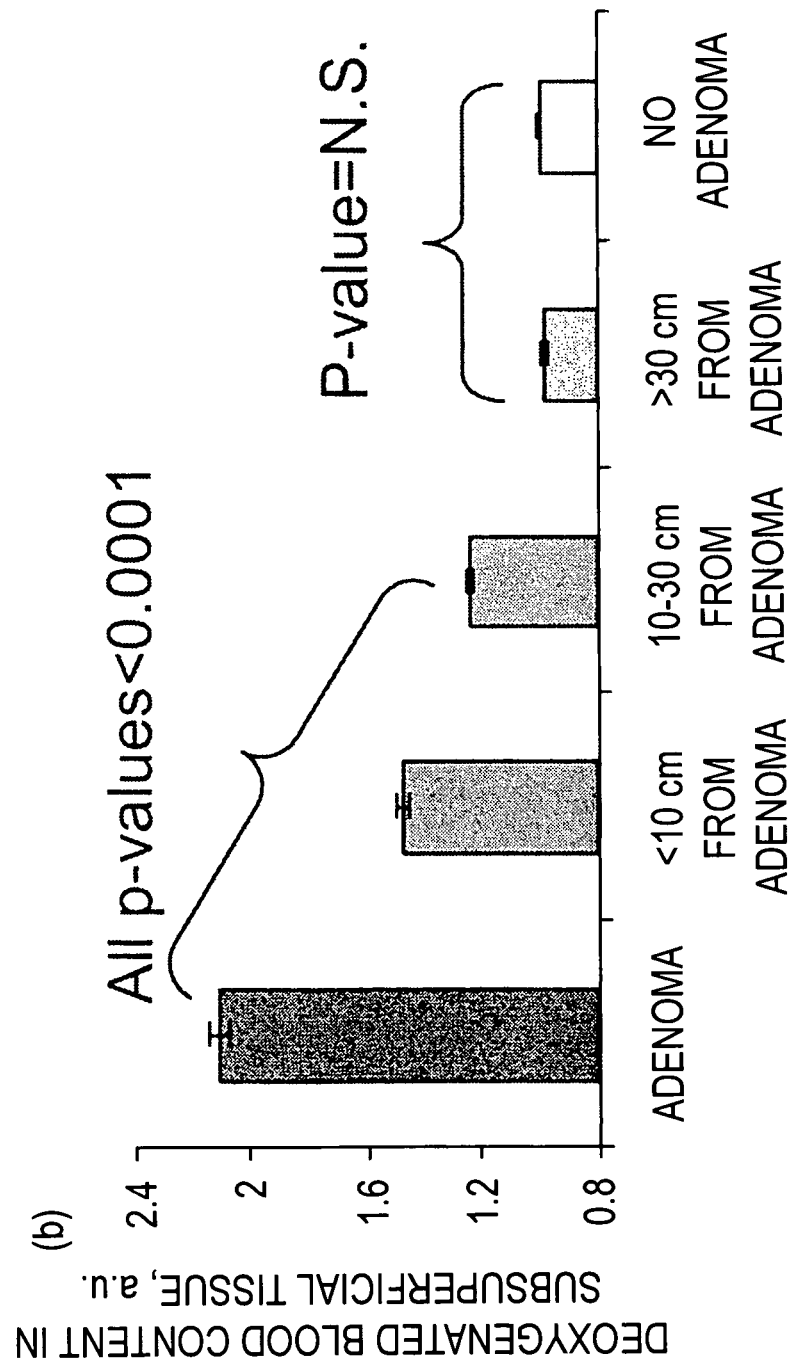
Figure 6D:
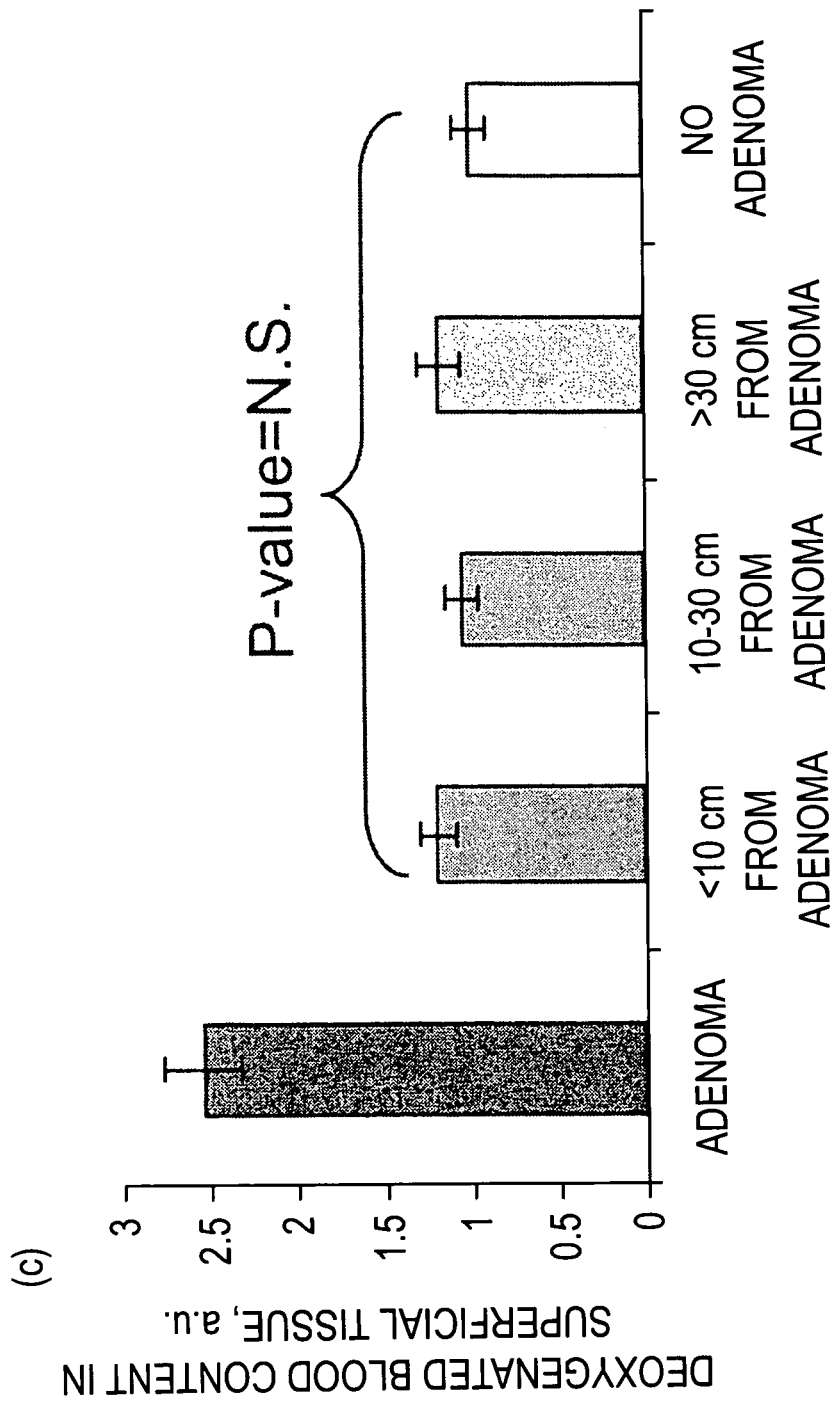

Our data (FIG. 6) demonstrate a marked augmentation of blood content in the uninvolved (endoscopically and histologically normal) colonic mucosal in patients with adenomas compared to the control subjects. Importantly, EIBS progressively increased when approaching a neoplastic lesion. Indeed, EIBS was noticeable about 30 cm from the location of the adenoma and progressed at 10 cm from the lesion and at the site of the lesion itself. It is this property of EIBS that may guide an endoscopist to identify high-risk colonic segments. EIBS in superficial tissue was observed even for locations >30 cm away from an adenoma (in colonic segments other than the one where the adenomas were found) (FIG. 6(a)). For comparison, EIBS in subsuperficial tissue was more localized and was observed only for distances <30 cm (FIG. 6(b)). This is consistent with our ex vivo data demonstrating that the spatial extend of EIBS decreases with tissue depth. Finally, FIG. 6(c) demonstrates that hyperplastic polyps do not result in EIBS outside their extend. This is also a promising result as it indicates that the absence of EIBS outside a polyp can be used to determine if a polyp is adenomatous or hyperplastic during the colonoscopy or other endoscopic procedure.

The performance characteristics of EIBS gradient to distinguish colonic segments with and without advanced adenomas are shown in Table 2. These characteristics are encouraging, particularly since because no other currently available technique enables sensing presence of adenomas by analysis of tissue outside the spatial extend of an adenoma. While characterizing the age of an adenoma is not possible, factoring the age of the person may be useful since as one ages microvascular blood content goes down in controls (neoplasia free).

TABLE 2

EIBS localization of advanced adenomas in humans by in vivo assessment of EIBS 10-30 cm from an adenoma (i.e., readings from a segment where an adenoma is located).

| | |
|---|---|
| Sensitivity | 100% |
| Specificity | 70% |

The performance characteristics of EIBS gradient to distinguish colonic segments with and without adenomas (as compared to advanced adenoma's above), as well as to differentiate between a tissue site located within 10 cm from the adenoma and between 10 and 30 cm, are shown in Table 3 below.

TABLE 3

| | Sensitivity | Specificity | | |
|---|---|---|---|---|
| vs. 10-30 cm from adenoma | 95% | 68% | 72% | 6% |
| with adenoma vs. normal control | 89% | 79% | 87% | 0% |
| vs. normal control | 97% | 92% | 89% | 6% |

The diagnostic performance of EIBS is also superior to conventional CRC screening techniques. For instance, a recent study demonstrated that FOBT and fecal DNA analysis had a sensitivity of 10.8% and 18.2%, respectively, and the sensitivity and positive predictive value of flexible sigmoidoscopy was reported to be only 52% and 6%, respectively. Furthermore, the analysis of our in vivo data showed that there was minor variation in microvascular blood content among the three colonic segments in control subjects, males vs. females, and patients of different age (from 40 to 80 years old). The accuracy of EIBS-based colonoscopy guidance may be improved by accounting for these variations.

Non-Optics Confirmation of EIBS.

Figure 7:
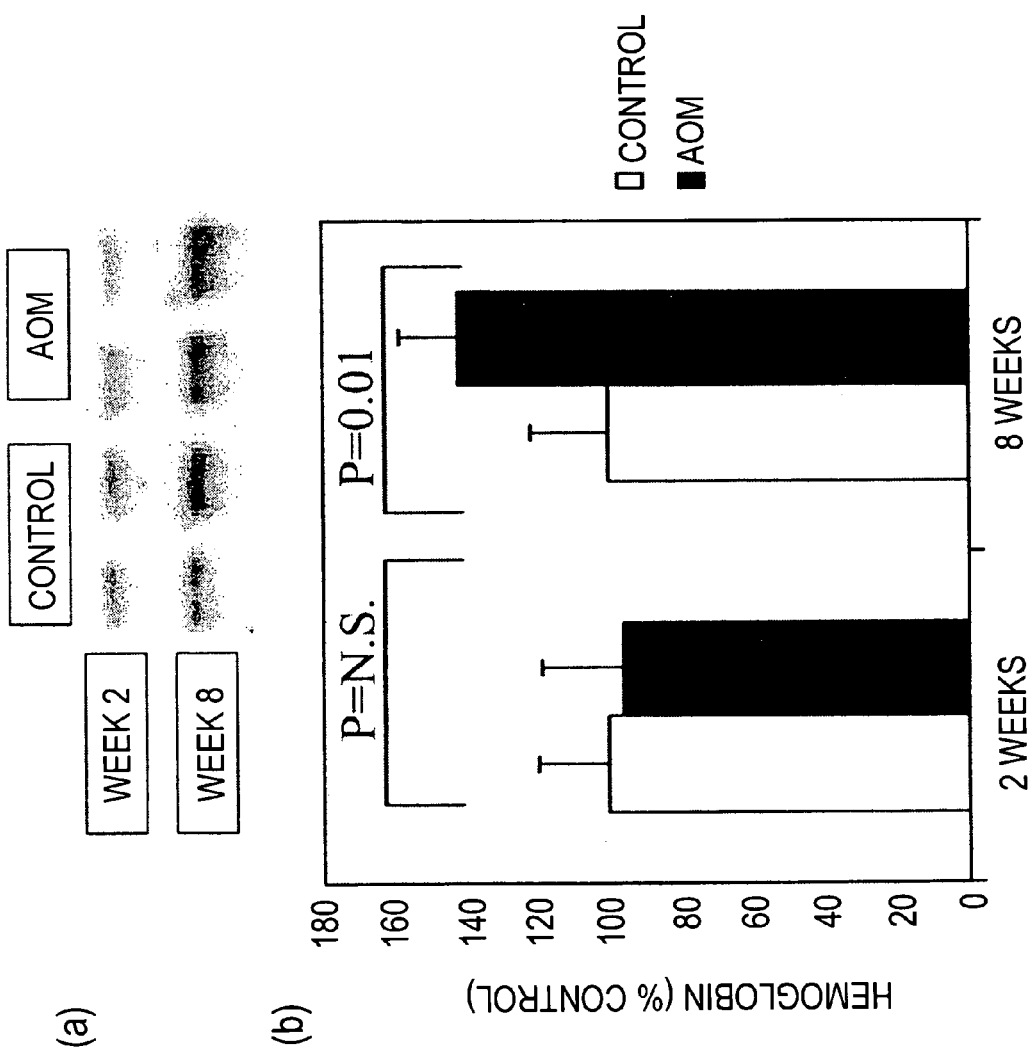
FIG. 7 shows the data confirming the phenomenon of EIBS in AOM-treated rats by Western blot. Although Western blot clearly shows EIBS 8 weeks after initiation of carcinogenesis (i.e., aberrant crypt foci (ACF), pre-adenoma stage of colon carcinogenesis), the sensitivity and accuracy of Western blot was not sufficient to measure EIBS in pre-ACF and stage (two weeks after initiation of carcinogenesis). For comparison, the disclosed optics approach has sensitivity sufficient enough to detect EIBS at this earliest time point.

We also wanted to confirm EIBS by use of a non-optics methodology. We used Western blotting and evaluated blood content in the mucosa/submucosa in AOM-treated and control rats. The distal colons of AOM-treated and age-matched control rats were gently scraped. Mucosal homogenates were made and 25 µg of protein was separated on a 10% SDS-PAGE gel, transferred to PDVF membranes and blocked with 5% non-fat milk. Membranes were probed with a polyclonal antibody to hemoglobin (1:300 dilution/overnight at 4 C, Santa Cruz Biotechnology) and xerograms were developed with enhanced chemiluminescence and quantitated with a laser densitometer. One clear band at the appropriate molecular weight was noted (68 kDa) as shown in FIG. 7(a). This band did not appear on any negative controls (including lysates of two colon cancer cell lines HT-29 and HCT-116 and rat samples probed with secondary antibody alone). Quantitation of the immunoblot analysis (relative to age-matched controls) is demonstrated in FIG. 7(b). As can be seen, there is a significant increase in hemoglobin content in the distal colon at 8 weeks (p=0.01). Blots were stripped and probed for $\beta$-actin to confirm uniform protein loading (data not shown).

This provides critical non-optics corroboration of EIBS. Moreover, it underscores the relative lack of sensitivity of non-optics based technologies. For instance, while the 8-week data are significant, the increase is much less dramatic than the 3-fold augmentation of EIBS noted with spectroscopy. Moreover, mucosal blood content analysis failed to reveal a difference at 2 weeks despite highly significant changes seen with spectroscopic analysis. We believe that this dramatic sensitivity of spectroscopic analysis is related in part to its ability to precisely assay just the vasculature. Mucosal scrapings, on the other hand, no matter how gentle, probably samples some of the larger blood vessels in the submucosa. Since we believe that EIBS in the histologically normal mucosa is primarily a microvascular phenomenon, assaying the deeper larger blood vessels can easily obscure the subtle early changes in the microvasculature.

Further Applications of EIBS

Figure 8:
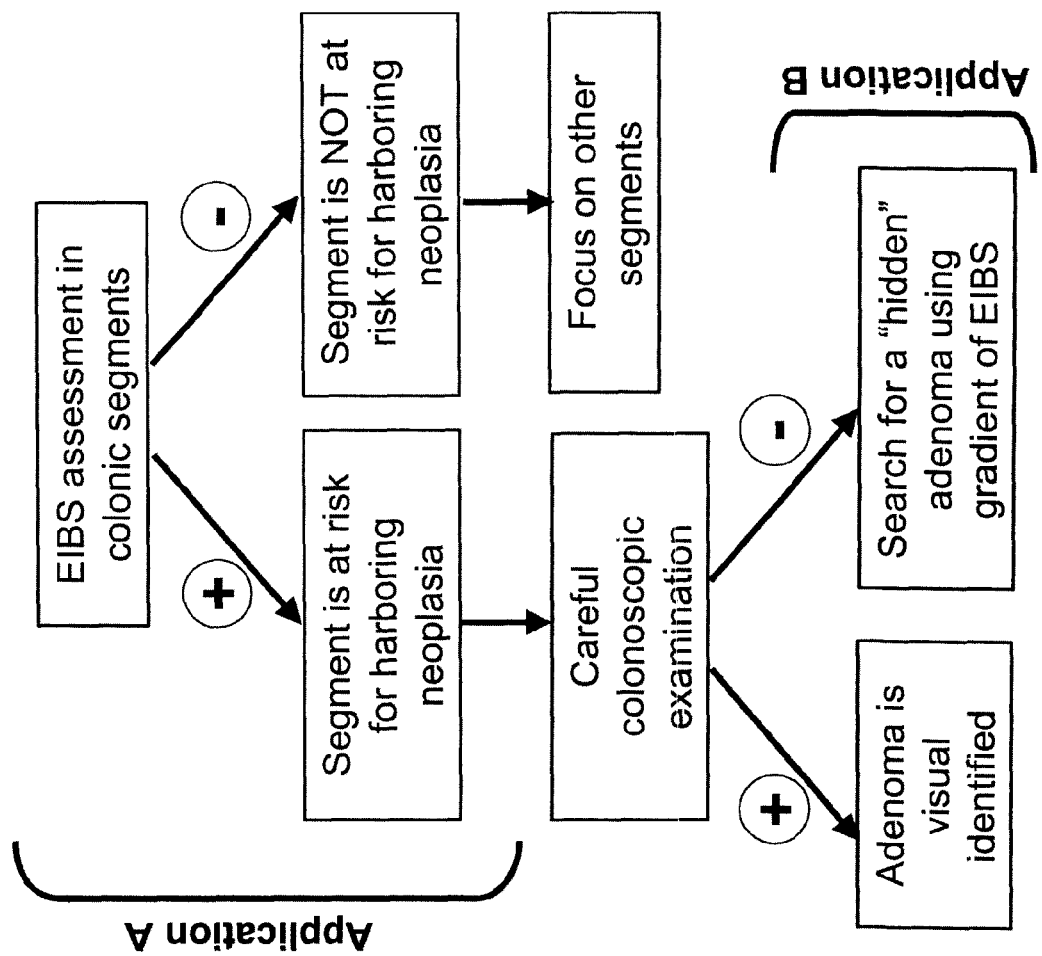
FIG. 8 shows according to one embodiment of the present invention a methodology of EIBS-assisted colonoscopy.

Using 4D-ELF or 2D-ELF (as described hereinafter) and polarization gated spectroscopy, this EIBS biological phenomenon in colonic mucosa in early CRC can be used for early stage detection of lesions. Importantly, spatially, EIBS extended outside the location of a neoplastic lesion (within at least ~⅓ of colon from the lesion and beyond, depending on the depth of tissue) and its magnitude increased in the proximity to adenomas. Thus, our data showed that EIBS allowed remarkably accurate determination as to whether a given colonic segment harbors adenoma and could be used to indicate to an endoscopist the proximity of an adenoma. The methodology is to use EIBS to reduce colonoscopic miss rate (15-20% for adenomas and 6-12% for advanced adenomas) by guiding colonoscopy. We propose various applications of EIBS, two of which are illustrated as Application A and Application B in FIG. 8.

Application A:

EIBS assessed from a given colonic segment will signal endoscopist that this segment is at risk for harboring adenomas and requires more rigorous colonoscopic evaluation. If a segment is not at-risk as determined by EIBS measurements, an endoscopist may make decision to focus on other colonic segments that may require more intense examination.

Application B:

If adenoma is not readily visualized within this segment, increase magnitude of EIBS with approaching a lesion will guide an endoscopist in search for a hidden neoplasia.

Other usages of EIBS, Application C:

EMS can be assessed from distal colon during flexible sigmoidoscopy to assist in detection of the presence of adenomas and tumors in the proximal colon. As is known, a sigmoidoscopy is similar to a colonoscopy but examines only the lower colon and rectum. In such a procedure, the EIBS probe can be used in addition to the sigmoidoscopy probe to obtain the EIBS data. Furthermore, EIBS can be assessed from the rectum either via flexible sigmoidoscopy, a stand-alone fiber-optic probe, or a probe as part of an endoscopic device to assist in detection of the presence of adenomas and tumors in the other parts of colon.

Other usages of EIBS, Application D:

EIBS can be assessed during colonoscopy, flexible sigmoidoscopy, or other endoscopic procedures to predict the development of future precancerous or cancerous lesions and, thus, assist in determining the schedule (e.g., frequency and time intervals) of future colonoscopies or flexible sigmoidoscopy procedures for a given patient.

Other usages of EIBS, in addition to the usages described above are within the intended scope of the invention, and particularly in conjunction with other diagnostic methods.

In addition to 4D-ELF and polarization gated spectroscopy, other spectroscopic techniques such as, 2D-ELF, enhanced backscattering and low-coherence enhanced backscattering (LEBS) spectroscopy, and OCT can also be used to practice the present invention.

For example, EIBS can be used in conjunction with a screening colonoscopy, in which case the EIBS probe can be used in addition to the colonoscopy probe to obtain the EIBS data.

Distinguishing Adenomatous Polyps and Hyperplastic Polyps

While adenomatous polyps engender EIBS, hyperplastic polyps do not. As such, this allows for the distinguishing between these two types of polyps during colonoscopy.

Diagnosis of tissue as either hyperplastic (also referred to as benign) or adenomatous (also referred to as neoplastic) using optical techniques has been termed "optical biopsy." This present embodiment is directed toward an optical biopsy of colonic adenomas, as it can be used as an adjunct to colonoscopy to guide an endoscopist if a particular polyp is hyperplastic (benign) or adenomatous. In particular, it has been observed that EIBS occurs, as discussed above, in regions surrounding an adenomatous polyp, but not a hyperplastic polyp, and the automated display indicating that the EIBS measurement in a region surrounding a polyp, as compared to a baseline EIBS reading, can be used as a measure to distinguish between an adenomatous polyp and a hyperplastic polyp. In particular, an EIBS reading taken with 10 cm of the polyp can accurately be used to conclude that the polyp is adenomatous versus hyperplastic.

Although an adenomatous polyp has to be removed, a hyperplastic polyp may be left in place. Altering a colonoscopy procedure to leave known hyperplastic polyps in place, as well as to distinguish more readily between a polyp that is a possible adenomatous poly or a hyperplastic polyp can reduce the time it takes to perform a colonoscopy, especially in patients with multiple polyps. The saved time could be used to perform a better surveillance of the colon, thus potentially reducing colonoscopic miss rate, i.e., the rate at which cancerous tissues are undetected during a colonoscopy. This new capability of EIBS, in combination with the above-described applications of EIBS as i) a risk-stratification tool (by identifying patients at risk for harboring colonic adenomas) and ii) a guide-to-colonoscopy tool (by identifying colonic segments likely to harbor adenomas), make the fiber-optic EIBS-detection a platform technology to improve colon cancer screening, diagnosis, and detection.

Example: A study was performed on 224 patients comprising 175 who were adenoma-free, 25 with non-advanced adenomas, 5 with advanced adenomas, and 19 with hyperplastic polyps. These patients, all undergoing colonoscopy, had, on average, 10 readings taken using a fiber-optic EIBS probe in the endoscopically normal mucosa within 10 cm from a polyp. None of the readings were taken from polyps. Our analysis showed that superficial (<100 μm) OHb and DHb were altered in subjects harboring adenomas compared to hyperplastic polyps (FIGS. 2(a, b)). The p-values for the OHb were as follows: advanced adenomas (AA) vs. hyperplastic polyps (HP), p=0.07, adenomas of any size (A) vs. HP, p=N.S. The p-values for the DHb were as follows: AA vs. HP, p=0.02, A vs. HP, p=0.004.

TABLE 4

In vivo diagnosis of adenomatous versus hyperplastic polyps via EIBS assessment in the normal mucosa mucosa 10 cm from a polyp

|  | HP vs. adenoma | HP vs. advanced adenoma |
|---|---|---|
| Area under ROC curve | 0.720 | 0.889 |
| Sensitivity | 73% | 100% |
| Specificity | 56% | 78% |

Table 4, provided above, shows that good diagnostic performance characteristics could be achieved when the OHb and DHb were combined into a simple prediction rule using logistics regression. To diagnose a polyp as either adenomatous or hyperplastic (benign) based on the analysis of mucosal microvasculature within 10 cm from a polyp, a prediction rule can be developed based on two markers: oxy-Hb and deoxy-Hb concentrations. For example, a prediction rule can be designed as follows. First, EIBS index was calculated as a linear combination of these two EIBS parameters. A binary diagnostic variable (no neoplasia=0, adenoma=1) was used to fit weighting coefficients, $\beta_1$ using logistic regression such that: EIBS index=Logit(p)=ln(p/(1−p))=$\beta_1 P_1 \beta_2 P_2$, where $P_1$ and $P_2$ are the OHb and DHb concentrations and p is the probability of a positive binary outcome (adenoma). Thus, the coefficients were determined empirically and defined the relationship between the EIBS index and the experimentally measured parameters. For example, the index to differentiate advanced adenomas and hyperplastic polyps was 2.62*OHb+ 2.37*DHb. (An approximate index OHb+DHb=total mucosal Hb concentration has a slightly lower but very similar diagnostic performance.) Following this, a diagnostic threshold value of the index was determined for OHb based on the receiver observer characteristics (ROC) curve to obtain a desirable balance between sensitivity and specificity. For example, 100% sensitivity and 78% specificity was achieved for the discrimination between advanced adenomas and hyperplastic polyps. We also assessed confounding by demographic factors including age and smoking history and found that these factors had no significant effect on the test outcome.

The foregoing description of the exemplary embodiments of the invention has been presented only for the purposes of illustration and description and is not intended to be exhaustive or to limit the invention to the precise forms disclosed. Many modifications and variations are possible in light of the above teachings.

What is claimed is:

1. A method of providing an indication that a living polyp within a human body is either adenomatous or hyperplastic, comprising:
   inserting an illumination probe such that a light source within the illumination probe is disposed in a location that is at a surface of a colon and contains the polyp;
   illuminating, at the location, tissue of the colon and microvasculature therein with light from the light source that is emitted from the probe around the polyp;
   detecting interacted light that results from the illuminating of the tissue as detected data, wherein the interacted light comprises light that has interacted with blood in the microvasculature that is within the tissue of the colon;
   estimating at least one of blood content and blood flow in the microvasculature using the detected data to obtain an estimation of the at least one of the blood content and the blood flow; and
   identifying the polyp as being either adenomatous or hyperplastic based on the estimation of the at least one of the blood content and the blood flow, the identifying of the polyp as being either adenomatous or hyperplastic comprising determining whether there is an increase in the estimation of the at least one of the blood content and the blood flow in the microvasculature.

2. The method according to claim 1, further comprising removing the polyp if the polyp is identified as being adenomatous, while not removing the polyp if the polyp is identified as being hyperplastic.

3. The method according to claim 1, further comprising:
   visually examining the polyp with light if the polyp is indicated as being adenomatous; and
   removing the polyp if the poly is indicated as being adenomatous.

4. The method according to claim 1, wherein the interacted light comprises light that is scattered by the blood in the microvasculature.

5. The method according to claim 1, wherein the interacted light comprises light that is scattered and absorbed by the blood in the microvasculature.

6. The method according to claim 1, wherein the interacted light comprises light that is absorbed by the blood in the microvasculature.

7. The method according to claim 1, wherein the illumination probe is inserted into an inner surface of the colon.

8. The method according to claim 1, wherein the detecting of the interacted light comprises detecting at least one component of the interacted light selected from the group consisting of co-polarized, cross-polarized, and unpolarized interacted light.

9. The method according to claim 8, wherein the blood content is estimated.

10. The method according to claim 9, wherein the blood content is estimated by estimating a concentration of red blood cells.

11. The method according to claim 9, wherein the blood content is estimated by estimating a concentration of hemoglobin.

12. The method according to claim 9, wherein the blood content is estimated by estimating a concentration of de-oxygenated hemoglobin.

13. The method according to claim 9, wherein the blood content is estimated by estimating a concentration of oxygenated hemoglobin.

14. The method according to claim 8, wherein the blood flow is estimated by estimating a rate of blood flow.

15. The method according to claim 9, wherein the blood content is estimated by estimating oxygen saturation in the blood.

16. The method according to claim 8, wherein the at least one of the blood content and the blood flow is estimated by estimating a statistic of the at least one of the blood content and the blood flow within an area of the tissue.

17. The method according to claim 16, wherein the statistic is selected from the group consisting of mean, average, median, standard deviation, maximal value, and minimal value.

18. The method according to claim 8, wherein the interacted light is detected from the surface of the colon to a submucosal layer.

19. The method according to claim 8, wherein the interacted light is detected from the surface of the colon to a mucosal layer.

20. The method according to claim 1, further comprising performing a screening colonoscopy during a same period of time as the inserting of the illumination probe, the illuminating of the tissue of the colon and the microvasculature therein, and the detecting of the interacted light.

21. The method according to claim 1, further comprising performing a sigmoidoscopy during a same period of time as the inserting of the illumination probe, the illuminating of the tissue of the colon and the microvasculature therein, and the detecting of the interacted light.

22. The method according to claim 1, wherein the inserting of the illumination probe, the illuminating of the tissue of the colon and the microvasculature therein, and the detecting of the interacted light are performed using a stand-alone probe.

23. The method according to claim 1, wherein the inserting of the illumination probe, the illuminating of the tissue of the colon and the microvasculature therein, and the detecting of the interacted light are performed using a probe disposed at least partially within an endoscopic device.

24. The method according to claim 1, wherein the identifying of the polyp as being either adenomatous or hyperplastic comprises comparing the estimation of the blood content with a baseline blood content.

25. The method according to claim 24, further comprising establishing the baseline blood content.

26. The method according to claim 25, further comprising establishing the baseline blood content based upon measurements of blood content of a region surrounding the colon.

27. The method according to claim 25, further comprising establishing the baseline blood content based upon measurements of blood content of a plurality of bodies other than the body.

28. The method according to claim 25, further comprising establishing the baseline blood content based upon measurements of blood content of the body.

29. The method according to claim 1, wherein the blood content is estimated.

30. The method according to claim 29, wherein the blood content is estimated by estimating a concentration of red blood cells.

31. The method according to claim 29, wherein the blood content is estimated by estimating a concentration of hemoglobin.

32. The method according to claim 29, wherein the blood content is estimated by estimating a concentration of de-oxygenated hemoglobin.

33. The method according to claim 29, wherein the blood content is estimated by estimating a concentration of oxygenated hemoglobin.

34. The method according to claim 1, wherein the blood flow is estimated by estimating a rate of blood flow.

35. The method according to claim 29, wherein the blood content is estimated by estimating oxygen saturation in the blood.

36. The method according to claim 1, wherein the at least one of the blood content and the blood flow is estimated by estimating a statistic of the at least one of the blood content and the blood flow within an area of the tissue.

37. The method according to claim 36, wherein the statistic is selected from the group consisting of mean, average, median, standard deviation, maximal value, and minimal value.

* * * * *